(12) United States Patent
Colomb et al.

(10) Patent No.: US 10,080,852 B2
(45) Date of Patent: Sep. 25, 2018

(54) FLUID DISPENSER DEVICE WITH BELLOWS

(71) Applicant: APTAR FRANCE SAS, Le Neubourg (FR)

(72) Inventors: Arnaud Colomb, Verneuil sur Seine (FR); Matthieu Baillet, Bonsecours (FR)

(73) Assignee: APTAR FRANCE SAS, Le Neubourg (FR)

( * ) Notice: Subject to any disclaimer, the term of this patent is extended or adjusted under 35 U.S.C. 154(b) by 886 days.

(21) Appl. No.: 14/397,502

(22) PCT Filed: May 22, 2013

(86) PCT No.: PCT/FR2013/051110
§ 371 (c)(1),
(2) Date: Oct. 28, 2014

(87) PCT Pub. No.: WO2013/175120
PCT Pub. Date: Nov. 28, 2013

(65) Prior Publication Data
US 2015/0128938 A1    May 14, 2015

(30) Foreign Application Priority Data
May 24, 2012 (FR) ..................................... 12 54784

(51) Int. Cl.
*A61M 15/00* (2006.01)
*A61M 16/00* (2006.01)

(52) U.S. Cl.
CPC ...... *A61M 15/0058* (2014.02); *A61M 15/007* (2014.02); *A61M 15/0021* (2014.02);
(Continued)

(58) Field of Classification Search
CPC .. A61M 11/00; A61M 11/006; A61M 11/007; A61M 11/008; A61M 11/02;
(Continued)

(56) References Cited

U.S. PATENT DOCUMENTS 2,876,979 A * 3/1959 Barbera ................. F16F 13/00
267/140.11
2,886,033 A * 5/1959 Gagnan .................. A62B 9/022
128/204.28
(Continued)

FOREIGN PATENT DOCUMENTS

DE    100 11 717 A1    9/2001
FR    2 881 117 A1    7/2006
(Continued)

OTHER PUBLICATIONS

International Search Report for PCT/FR2013/051110 dated Nov. 12, 2013 [PCT/ISA/210].
(Continued)

*Primary Examiner* — Kathryn E Ditmer
(74) *Attorney, Agent, or Firm* — Sughrue Mion, PLLC

(57) ABSTRACT

A fluid dispenser device including a body and a reservoir, and an opening mechanism. The device includes an inhalation piece and an inhalation trigger system that has a deformable air chamber and a trigger element, such that during inhalation through the inhalation piece, the air chamber is deformed and the trigger element actuates the opening mechanism. The air chamber has a deformable side body; an open first end including a peripheral edge that surrounds an opening forming the inlet of the hollow pouch; and a second end forming the bottom of the hollow pouch. The said second end includes a connection mechanism for connecting the air chamber to the trigger element. The side body is in the form of a bellows having bellows portions arranged axially one after another, the bellows-forming side body has
(Continued)

bellows portions having outside and/or inside diameters that are different.

16 Claims, 4 Drawing Sheets

(52) U.S. Cl.
CPC .... *A61M 15/0026* (2014.02); *A61M 15/0045* (2013.01); *A61M 15/0051* (2014.02); *A61M 15/0055* (2014.02); *A61M 15/0071* (2014.02); *A61M 15/0081* (2014.02); *A61M 15/0086* (2013.01); *A61M 15/0091* (2013.01); *A61M 16/0075* (2013.01); *A61M 15/0073* (2014.02); *A61M 15/0075* (2014.02); *A61M 2202/064* (2013.01)

(58) Field of Classification Search
CPC .............. A61M 15/00; A61M 15/0005; A61M 15/0006; A61M 15/0028; A61M 15/003; A61M 15/0035; A61M 15/0036; A61M 15/0038; A61M 15/004; A61M 15/0041; A61M 15/0045; A61M 15/0051; A61M 15/0091; A61M 15/0096; A61M 16/0075
See application file for complete search history.

(56) References Cited

U.S. PATENT DOCUMENTS

| | | | | |
|---|---|---|---|---|
| 3,340,869 A | * | 9/1967 | Bane ...................... | A61M 3/00 206/364 |
| 3,530,857 A | * | 9/1970 | Lothar ..................... | A62B 7/02 128/205.13 |
| 3,973,700 A | * | 8/1976 | Schmidt ................ | B05B 11/303 222/153.13 |
| 4,821,713 A | * | 4/1989 | Bauman ............ | A61M 16/0078 128/205.13 |
| 5,518,147 A | * | 5/1996 | Peterson ............. | B05B 11/3035 222/153.07 |
| 6,332,876 B1 | * | 12/2001 | Poynter .................. | A61M 5/282 604/212 |
| 6,866,039 B1 | * | 3/2005 | Wright .............. | A61M 15/0028 128/203.15 |
| 7,246,723 B2 | * | 7/2007 | Santagiuliana ..... | B05B 11/3008 222/190 |
| 7,383,736 B2 | * | 6/2008 | Esnouf ................ | A61M 16/044 128/205.23 |
| 2007/0157991 A1 | * | 7/2007 | Robertson ............ | A47K 5/1208 141/360 |
| 2008/0099015 A1 | * | 5/2008 | Pocock ............. | A61M 15/0045 128/203.15 |
| 2009/0283095 A1 | | 11/2009 | Pocock et al. | |
| 2010/0163042 A1 | * | 7/2010 | Bhowmick ........ | A61M 15/0045 128/203.15 |
| 2010/0307492 A1 | * | 12/2010 | Fabien .............. | A61M 15/0045 128/203.15 |
| 2011/0203589 A1 | * | 8/2011 | Fenton ............. | A61M 16/0072 128/205.13 |
| 2013/0019689 A1 | * | 1/2013 | Slocum ................... | G01L 7/061 73/729.1 |
| 2013/0139815 A1 | | 6/2013 | Colomb et al. | |

FOREIGN PATENT DOCUMENTS

| | | | | |
|---|---|---|---|---|
| JP | 2007225093 A | * | 9/2007 | .............. E05F 5/022 |
| WO | 2008/012458 A2 | | 1/2008 | |
| WO | 2011/154659 A1 | | 12/2011 | |

OTHER PUBLICATIONS

International Preliminary Report of Patentability dated Nov. 25, 2014 from the International Searching Authority in counterpart Application No. PCT/FR2013/051110.

\* cited by examiner

FLUID DISPENSER DEVICE WITH BELLOWS

CROSS REFERENCE TO RELATED APPLICATIONS

This application is a National Stage of International Application No. PCT/FR2013/051110, filed on May 22, 2013, which claims priority from French Patent Application No. 1254784, filed on May 24, 2012, the contents of all of which are incorporated herein by reference in their entirety.

The present invention relates to a fluid dispenser device, and more particularly to a dry-powder inhaler.

Inhalers are well known in the prior art. Various types exist. A first type of inhaler contains a reservoir receiving many doses of powder, the inhaler being provided with metering means making it possible, on each actuation, to remove one dose of said powder from the reservoir, so as to bring said dose into an expulsion duct in order to be dispensed to the user. Inhalers including individual reservoirs, such as capsules, that are loaded into the inhaler just before said reservoir is used are also described in the prior art. The advantage of such devices is that it is not necessary to store all of the doses inside the appliance, such that said appliance can be compact. However, the inhaler is more difficult to use, since the user is obliged to load a capsule into the inhaler before each use. Another type of inhaler consists in placing the doses of powder in individual predosed reservoirs, then in opening one of the reservoirs each time the inhaler is actuated. That implementation seals the powder more effectively since each dose is opened only when it is about to be expelled. In order to make such individual reservoirs, various techniques have already been proposed, such as an elongate blister strip or blisters disposed on a rotary circular disk. All existing types of inhalers, including those described above, present both advantages and drawbacks associated with their structures and with their types of operation. Thus, with certain inhalers, there is the problem of metering accuracy and reproducibility on each actuation. In addition, the effectiveness of the dispensing, i.e. the fraction of the dose that effectively penetrates into the user's lungs in order to have a beneficial therapeutic effect, is also a problem that exists with a certain number of inhalers. A solution for solving that specific problem has been to synchronize the expulsion of the dose with the inhalation of the patient. Once again, that can create drawbacks, in particular in that type of device, the dose is generally initially loaded into an expulsion duct before inhalation, then expulsion is synchronized with inhalation. That means that if the user drops, shakes, or manipulates the inhaler in an undesirable or inappropriate manner between the moment when the user loads the dose (either from a multidose reservoir or from an individual reservoir) and the moment when the user inhales, then the user risks losing all or part of the dose, with said dose possibly being spread about inside the appliance. In that event, there can exist a high risk of overdosing the next time the device is used. The user who realizes that the dose is not complete will load a new dose into the appliance, and while the new dose is being inhaled, a fraction of the preceding dose that was lost in the appliance could thus be expelled at the same time as the new dose, thereby causing an overdose. In the treatments envisaged, such overdosing can be very harmful, and the authorities in all countries are issuing ever-stricter requirements to limit the risk of overdosing as much as possible. Documents FR-2 881 117, WO 2008/012458, WO 2011/154659, and DE 100 11 717 describe prior-art devices.

An object of the present invention is to provide a fluid dispenser device, in particular a dry-powder inhaler, that does not have the above-mentioned drawbacks.

In particular, an object of the present invention is to provide such a device that is simple and inexpensive to manufacture and to assemble, that can be used reliably, guaranteeing metering accuracy and reproducibility on each actuation, providing an optimum yield with regard to the effectiveness of the treatment, by making it possible to dispense a substantial fraction of the dose to the zones to be treated, in particular the lungs, avoiding, in safe and effective manner, any risk of overdosing, and that is as compact as possible, while guaranteeing sealing and absolute integrity of all of the doses up to their expulsion.

The present invention thus provides a fluid dispenser device including a body and at least one individual reservoir containing a single dose of fluid, such as powder, opening means being provided for opening an individual reservoir each time the device is actuated, the device including an inhalation piece and an inhalation trigger system that comprises a deformable air chamber that co-operates with said inhalation piece, and a trigger element that co-operates with said air chamber, such that during inhalation through said inhalation piece, said air chamber is deformed and said trigger element actuates said opening means, so that a reservoir is opened by said opening means, said air chamber comprising: a deformable side body; an open first end including a peripheral edge that surrounds an opening forming the inlet of said hollow pouch; and a second end forming the bottom of said hollow pouch; said second end including connection means for connecting said air chamber to said trigger element, said side body being in the form of a bellows comprising a plurality of bellows portions, advantageously six, arranged axially one after another, said bellows-forming side body comprising bellows portions having outside and/or inside diameters that are different.

Advantageously, said air chamber is a blind hollow pouch including a closed second end that forms the bottom of said hollow pouch.

Advantageously, the first bellows portion adjacent to said opening has an outside diameter that is smaller than the outside diameter of the second bellows portion adjacent to said first bellows portion.

Advantageously, said air chamber is connected to said inhalation piece and to a dispenser chamber that receives the dose of fluid contained in a reservoir after it has been opened into the inhalation flow path, said dispenser chamber containing at least one movable ball.

Advantageously, the device includes movable support means that are adapted to move an individual reservoir against said opening means on each actuation, said movable support means being displaceable between a non-dispensing position and a dispensing position, said movable support means being urged towards their dispensing position by resilient means, such as a spring or a spring blade, and being held in their non-dispensing position by blocking means that are released by the user inhaling.

Advantageously, said trigger element co-operates with said blocking means so as to release said movable support means, which, once released, urge a reservoir against said opening means.

Advantageously, said movable support means support a guide wheel, the reservoirs being made in the form of an elongate strip comprising a plurality of individual reservoirs disposed one behind another, said guide wheel causing said strip to advance each time the device is actuated.

Advantageously, said opening means include a perforator element that is adapted to cut a closure wall of the reservoir in such a manner that the cut portion(s) does/do not obstruct the opening(s) that is/are formed.

Advantageously, said air chamber is made of silicone rubber.

Advantageously, said connection means for connecting said air chamber to said trigger element comprise a projection that is formed on the outside of said deformable air chamber, said projection being snap-fastened on said trigger element while the device is being assembled.

Advantageously, said projection is snap-fastened in a hole of the trigger element.

Advantageously, said peripheral edge of the air chamber is heat-sealed, in particular by ultrasound, on a portion of said body and/or overmolded on said portion of said body.

These characteristics and advantages and others of the present invention appear more clearly from the following detailed description, given by way of non-limiting example, and with reference to the accompanying drawing, and in which.

Figure 1:
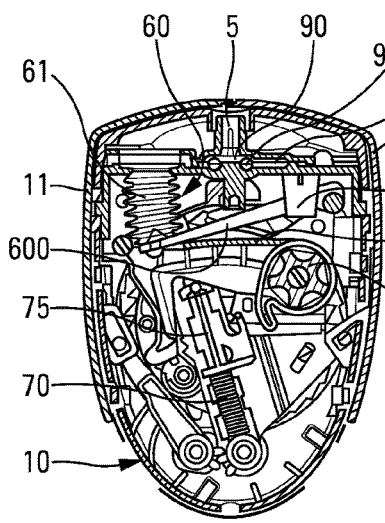
FIGS. 1 to 3 are diagrammatic section views of a dispenser device in an advantageous embodiment of the invention, respectively before opening, after opening but before inhalation, and after inhalation.

The figures show an advantageous embodiment of a dry-powder inhaler. The inhaler includes a body 10 on which there can be slidably mounted two cover-forming portions 11, 12 that are adapted to be opened so as to open and prime the device. The body 10 can be approximately rounded in shape, as shown in the figures, but it could be of any other appropriate shape. The body 10 includes a mouthpiece or inhalation piece 5 that defines a dispenser orifice through which the user inhales while the device is being actuated. The orifice is typically arranged approximately at the center of the top portion of the body (in the position shown in the drawings). The covers 11, 12 can open by pivoting about a common pivot axis, or about two parallel axes by being meshed together. Any other opening means for opening the device can be envisaged. In a variant, the device could include only a single cover instead of two.

Inside the body 10 there is provided a strip (not shown for the sake of clarity) of individual reservoirs, also known as blisters, said strip being made in the form of an elongate strip on which the blisters are disposed one behind another, in manner known per se. The blister strip is advantageously constituted by a base layer or wall that forms the cavities receiving the doses of powder, and by a closure layer or wall that covers each of said blisters in sealed manner. Before first use, the blister strip can be rolled-up inside the body 10, preferably in a storage portion, and first strip displacement means 40, in particular rotary means, are provided for progressively unrolling the blister strip and for causing it to advance.

Second displacement means 50, in particular means that are mounted to pivot on the body 10, are provided for bringing a respective blister into a dispensing position each time the device is actuated. The second displacement means are advantageously mounted to pivot between a non-dispensing position and a dispensing position in which a blister co-operates with said opening means.

The strip portion including the empty blisters is advantageously adapted to be rolled-up at another location of said body 10, preferably a reception portion, as described in greater detail below.

The inhaler includes blister opening means 80 (shown in part only for the sake of clarity) preferably comprising a perforator and/or cutter needle for perforating and/or cutting the closure layer of the blisters. Preferably, the opening means comprise a perforator element 80 that is stationary relative to the body 10, and against which a respective blister is displaced on each actuation by the second displacement means. The blister is thus perforated by said perforator element that penetrates into said blister so as to expel the powder by means of the user inhaling. Advantageously, the perforator element is adapted to cut a closure wall of the reservoir in such a manner that the cut portion(s) does/do not obstruct the opening(s) that is/are formed. Documents WO 2006/079750 and WO 2009/007640 describe such blister opening means, and they are thus incorporated in the present description by way of reference.

The first displacement means 40 are adapted to cause the blister strip to advance after each inhalation of the user. The second displacement means 50 are adapted to displace the blister to be emptied against said opening means during actuation, before each inhalation. The second displacement means can be urged by a resilient element 70, such as a spring or any other equivalent resilient element, said resilient element being suitable for being prestressed while the device is being opened.

Preferably, the first displacement means 40 are formed by an indexer wheel that receives and guides the blister strip. The description below is thus made with reference to such an indexer wheel 40. Turning the indexer wheel 40 causes the blister strip to advance. Before each inhalation, a full blister is always in a position facing the opening means 80. The second displacement means 50 can include a pivot member that is mounted to pivot about a pivot axis, said indexer wheel 40 advantageously being rotatably mounted on said pivot member.

An actuation cycle of the device can be as follows. During opening of the device, the two cover-forming lateral portions 11, 12 are moved away from each other by pivoting about the body so as to open the device and thus spring-load the device. In this position, the indexer wheel 40 cannot be displaced towards the perforator element 80, since the second displacement means 50 are held by appropriate blocking means (not shown for the sake of clarity). Documents WO 2009/077700 and WO 2009/136098 describe such blocking means, and they are thus incorporated in the present description by way of reference. While the user is inhaling through the mouthpiece, the blocking means are unblocked, thereby causing said indexer wheel 40 to move towards the needle, and thereby causing a blister to be opened.

As explained above, it is desirable for the opening means to be actuated by the user inhaling. In order to trigger the opening means by inhalation, an inhalation trigger system 60 is provided that advantageously comprises an air chamber 61 that is deformable under the effect of inhalation, the air chamber being adapted to release the blocking means. Inhalation by the user causes said deformable air-chamber to deform, thereby releasing said blocking means and enabling the second displacement means to be displaced, and therefore enabling a respective blister to be displaced towards its opening position. The blister is therefore opened only on inhalation, such that it is emptied simultaneously. Thus, there is no risk of any of the dose being lost between opening the blister and emptying it.

The inhaler further includes a dispenser or dispersion chamber 90 for receiving the dose of powder after a respective blister has been opened. The dispenser chamber is advantageously provided with at least one and preferably more beads 91 that are displaced inside said chamber 90 during inhalation, in particular so as to improve dispensing of the air and powder mixture after a blister has been opened, in order to increase the effectiveness of the device.

It can be advantageous for the opening means, in particular for the perforator element, to be formed directly on said dispenser chamber, e.g. at the end of a channel 95 leading to said chamber 90.

After inhalation, when the user closes the device, all of the components return to their initial, rest positions. The device is thus ready for a new utilization cycle.

In an advantageous aspect of the inhaler, the blisters are formed on a flexible elongate strip that, initially, is mainly stored in the form of a roll in a storage housing inside the body 10 of the device. Advantageously, the rolled-up blister strip is held by inner walls of said storage housing without its rear end (rear in the advancement direction of the blister strip) being fastened relative to said body 10, thereby enabling the blister-strip roll to be assembled more easily inside the device.

The blister strip is displaced by means of the indexer wheel 40 that advantageously presents at least one and preferably more recesses, each having a shape that corresponds to the shape of the blisters. Thus, when the indexer wheel 40 turns, it causes the blister strip to advance.

Naturally, in a variant or in additional manner, it is possible to use other means for advancing the blister strip, e.g. providing a profile on the longitudinal lateral edges of the blister strip, said profile being adapted to co-operate with appropriate drive means. In addition, holes formed along the lateral edges of the blister strip could also be used to cause the blister strip to advance by means of sprocket wheels co-operating with said holes.

After opening one or more blisters, the blister-strip portion with the empty blisters must be suitable for being stored in easy and compact manner in the device, while avoiding any risk of blockage. Advantageously, the used blister strip is rolled-up automatically, once again forming a roll.

In still another aspect of the inhaler, a dose counter or indicator device (not shown for the sake of clarity) is also provided. The device may include numbers or symbols that are marked directly on the blister strip, and that are visible through an appropriate window in the body 10 of the device. In a variant, it is possible to envisage using a counter with one or more rotary disks or rings including numbers or symbols. Documents WO 2008/012458 and WO 2011/154659 describe such counters, and they are thus incorporated in the present description by way of reference. An object of the invention is to avoid counting doses that have not been dispensed, e.g. in the event of a manipulation error, or an incomplete manipulation of the device. It is thus desirable that the counter or indicator is actuated only once the user has inhaled, since it is this inhalation that makes it possible for the blister to open and the dose contained therein to be dispensed. Advantageously, the counter is thus actuated after inhalation, when the user closes the device.

Figure 2:
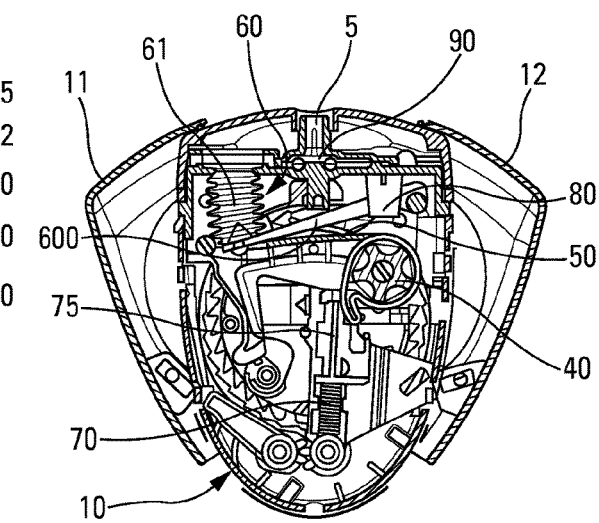
Figure 3:
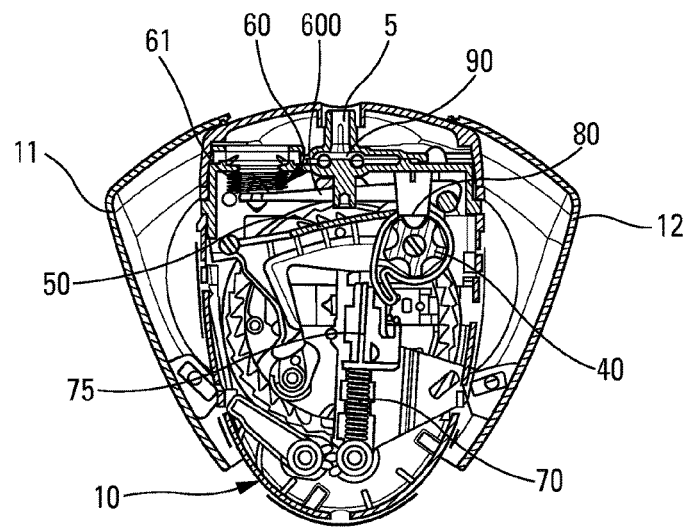

FIGS. 1 to 3 show an opening and inhalation cycle of the device.

The movable cover element 12 is secured to a cocking member 75 that can slide in an appropriate housing. The cocking member 75 thus advantageously pivots relative to said body 10 together with the cover element 12. The cocking member 75 may be moved against a spring 70, advantageously a coil spring, that is arranged in said housing. The cocking member 75 is thus connected at one end to said spring 70, and at the other end it co-operates with the second displacement means, in particular with a pivot member 50 that is mounted to pivot on the body 10, and on which the indexer wheel 40 is fastened is rotary manner.

When the movable cover element 12 is opened, as shown in FIG. 1 (closed position) and in FIG. 2 (open position), the cocking member 75 is displaced in its housing, compressing the spring 70. The pivot member 50 of the second displacement means is itself prevented from moving by the above-mentioned blocking means that are released only at the moment of inhalation. Thus, in the absence of any inhalation in the open position in FIG. 2, closing the cover elements 11, 12 would merely cause the cocking member 75 to return to its rest position and the spring 70 to decompress.

Advantageously, in its portion in contact with the pivot member 50, the cocking member 75 includes a rounded portion, such as a ball-shaped end, so as to encourage the cocking member to slide over the surface with which it co-operates.

Thus, by opening the inhaler, the user primes the system (FIGS. 1 and 2). If the user does not inhale and closes the inhaler, said inhaler merely returns to its start position without displacing the blister strip or the blocking means. There is thus no risk of a blister (and thus an active dose of substance) being lost by accidental or incomplete actuation in which the user does not inhale between opening and closing.

Opening the blister, emptying it, dispensing the powder into the lungs of the user, displacing the blister strip to bring a new full blister to face the opening means, and counting the dose are thus possible only if the user inhales.

The blocking means that block the second displacement means and in particular the pivot member that co-operates with the cocking member, are connected to the deformable air chamber 61 that is sensitive to the user inhaling, so that while the user is inhaling, said deformable air chamber deforms, causing said blocking means to be released. This enables said second displacement means to be displaced towards their dispensing position under the effect of the force exerted by the compressed spring 70 on the cocking member 75 that pushes against the pivot member 50. Such displacement causes a full blister to be opened and a dose to be dispensed.

Said deformable air chamber 61 of the inhalation trigger system is a hollow pouch comprising: a deformable side body 611; an open first end including a peripheral edge 62 that surrounds an opening forming the inlet of said hollow pouch; and a second end forming the bottom of said hollow pouch.

In the invention, said side body 611 is in the form of a bellows comprising a plurality of bellows portions 611a, 611b, 611c, etc., advantageously six, arranged axially one after another.

Figures 10, 11:
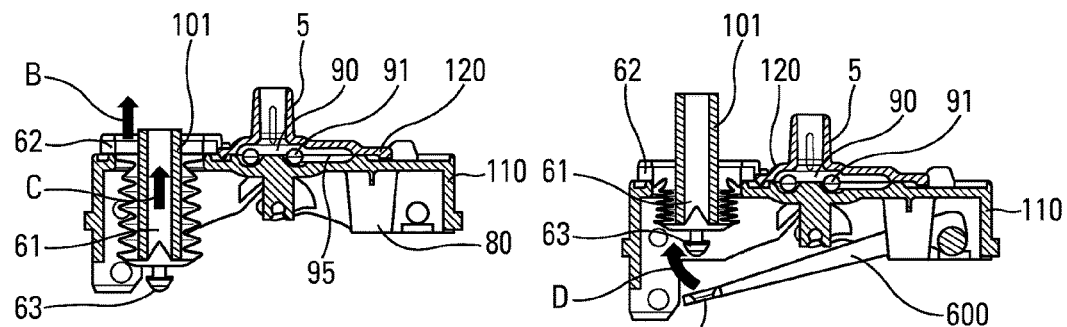
FIGS. 10 to 13 are views similar to the views in FIGS. 4 to 6, showing the stage of assembling the trigger element on the air chamber.

Said bellows 611 comprises one or more bellows portions having outside and/or inside diameters that are different. Advantageously, a first bellows portion 611a adjacent to said opening has an outside diameter that is smaller than the outside diameter of the second bellows portion 611b adjacent to said first bellows portion 611a. In particular, this has the effect of increasing the compression power of said bellows and of reducing the space that it occupies in its compressed position, as can be seen in particular in FIGS. 11 and 12, in which the first bellows portion 611a, when compressed, is deformed, in part, outside said opening defined by said peripheral edge 62. The smaller outside diameter thus releases space for the second bellows portion 611b, thereby making it possible to compress said bellows even more.

Naturally, one or more other bellows portions could also have an outside diameter that is different, in particular smaller, if necessary. In addition, provision could be made for one or more bellows portions to have inside diameters that are different.

The bellows shape provides several advantages. Thus, it defines a deformation force that is axial, and thus predictable and reproducible on each actuation. This makes it possible to obtain a narrower trigger range in the minimum inhalation rate required to trigger said inhalation trigger system, which range is advantageously reduced by about 50%. Furthermore, the bellows shape provides a spring effect that urges the deformable air pouch 61 towards its non-deformed position, and thus encourages the device to return to its rest position.

Advantageously, the deformable air chamber 61 is a blind hollow pouch, with said second end of the air chamber 61 being closed. This improves the sealing of the inhalation trigger system, avoiding leaks in the bottom of the air chamber.

A trigger element 600 co-operates with said air chamber 61, so that during inhalation through said inhalation piece 5, said air chamber 61 is deformed, displacing said trigger element 600 that then actuates said opening means 80, in particular by releasing the blocking means. Thus, during inhalation through the inhalation piece 5, a reservoir is opened by said opening means.

Said closed second end of the air chamber 61 includes connection means 63 for connecting said air chamber to said trigger element 600.

Advantageously, said trigger element is a rod that is connected firstly to said air chamber 61, and secondly to the blocking means. Thus, when the air chamber is deformed, it moves said rod, in particular by pivoting, thereby causing the blocking means to be released.

Said connection means 63 for connecting said air chamber 61 to said trigger element 600 preferably comprise a projection 63 that is formed on the outside of said deformable air chamber 61, said projection being snap-fastened on said trigger element while the device is being assembled, in particular in an opening 603 of said trigger element.

Advantageously, said peripheral edge 62 of the air chamber 61 is heat-sealed, in particular by ultrasound, on a portion 120 of said body 10 and/or overmolded on said portion 120 of said body 10.

The air chamber 61 is preferably made of silicone rubber, but other appropriate materials may be envisaged. The thickness of the membrane advantageously lies in the range 0.1 millimeters (mm) to 0.3 mm, preferably about 0.2 mm.

Figure 4:
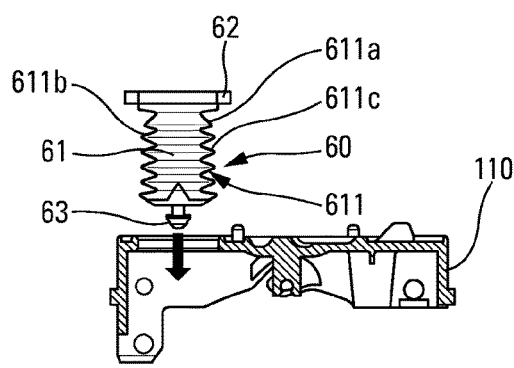
FIGS. 4 to 6 are diagrammatic and fragmentary cross-section views showing the stage of assembling the deformable air chamber, respectively before putting the air chamber into place on the support portion, after putting it into place, and after fastening the cover portion.
Figure 5:
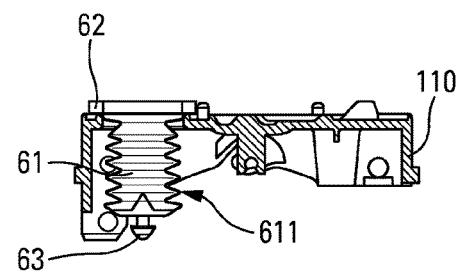
Figure 6:
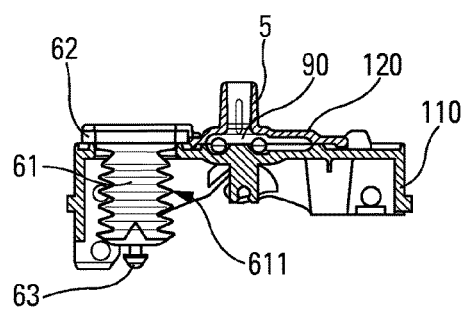

FIGS. 4 to 6 show an advantageous way of assembling the air chamber 61 in the body. In this variant, the air chamber 61 is arranged in a reception opening that is provided for this purpose in a first body portion 110, the peripheral edge 62 of the air chamber 61 coming to bear against the edge 118 of said reception opening, as can be seen in FIG. 5. A second body portion 120 is then assembled, in particular heat-sealed by ultrasound, on the first body portion 110, as shown in FIG. 6. The peripheral edge 62 of the air chamber is thus jammed between the two body portions 110, 120.

Figure 7:
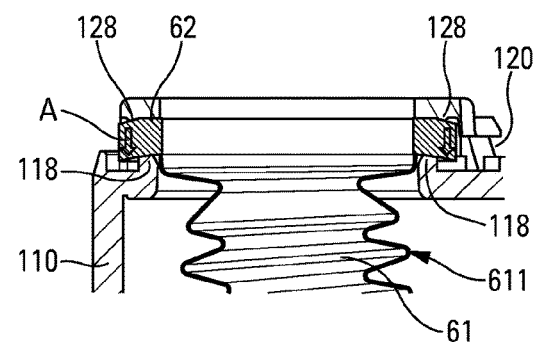
FIGS. 7 to 9 are diagrammatic views of a detail of three fastener variants for fastening the air chamber to said body.

Advantageously, in order to reinforce sealing during assembly, the second body portion 120 may include an axial projection or profile 128 that is offset radially outwards relative to the edge 118 against which the peripheral edge 62 of the air chamber bears. The projection 128 is adapted to deform said peripheral edge 62 of the air chamber 61 during assembly, as represented by arrow A in FIG. 7.

Figure 8:
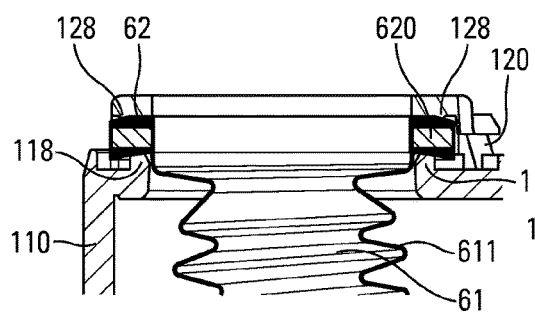

Optionally, as can be seen in FIG. 8, a rigid insert 620 may be arranged in said peripheral edge 62 so as to increase its stiffness and thus facilitate assembly thereof and improve its sealing.

Figure 9:
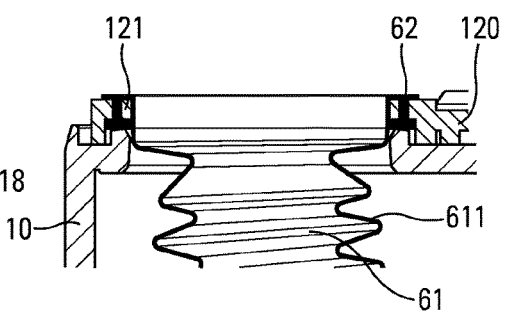

In a variant to the assembly in FIGS. 4 to 6, the peripheral edge 62 of the air chamber 61 may alternatively be fastened, in particular by overmolding, directly on the second body portion 120, as can be seen in FIG. 9. In this configuration, the air chamber 61 is assembled in the opening of the first body portion 110 when the second body portion 120 is fastened on said first body portion 110.

Figures 12, 13:
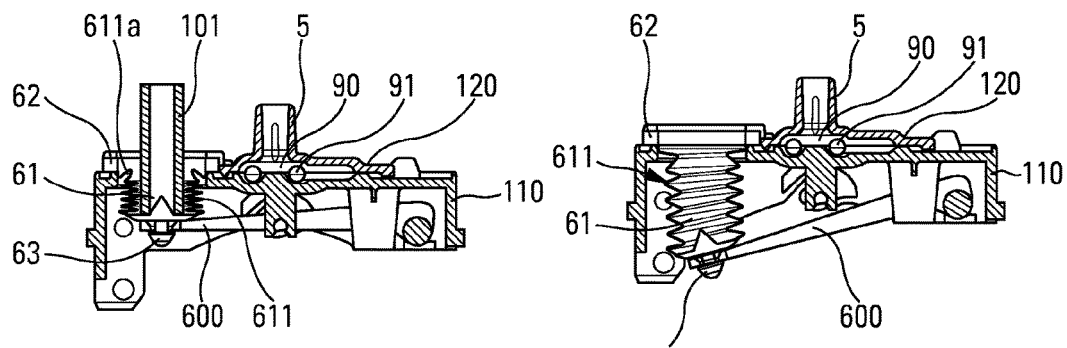
Figure 14:
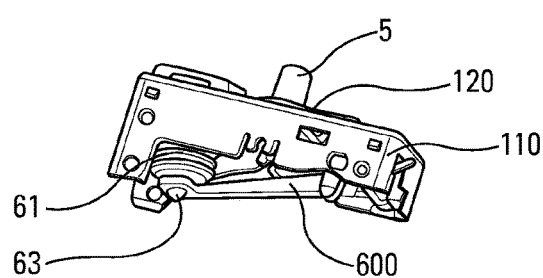
FIG. 14 is a diagrammatic and fragmentary perspective view similar to FIG. 13.

FIGS. 10 to 14 show the trigger element 600 being assembled on the air chamber 61. After assembling said air chamber 61 in the body, an assembly sleeve 101 is inserted into said air chamber 61, and said air chamber is deformed into its compressed position, in particular by suction, as represented by arrows B and C in FIG. 10. The trigger element 600, advantageously in the form of a pivotable rod, is then displaced along arrow D in FIG. 11, so as to snap-fasten a hole 603 of said rod on the projection 63 of the air chamber 61, as shown in FIG. 12. The suction in the air chamber 61 is then eliminated, and the assembly sleeve 101 is removed, thereby causing the air chamber 61 to deform towards its non-compressed state, and the rod 600 to pivot in return, as can be seen in FIGS. 13 and 14.

As can be seen in FIG. 13, the pivoting of the rod 600 causes the air chamber 61 to deform in a manner that is not exactly axial.

The use of a bellows shape optimizes the compression capacity of the air chamber, and presents the advantage of guaranteeing improved reproducibility of the deformation relative to the suction created during inhalation, thereby making the triggering of the device more reliable.

Figure 15:
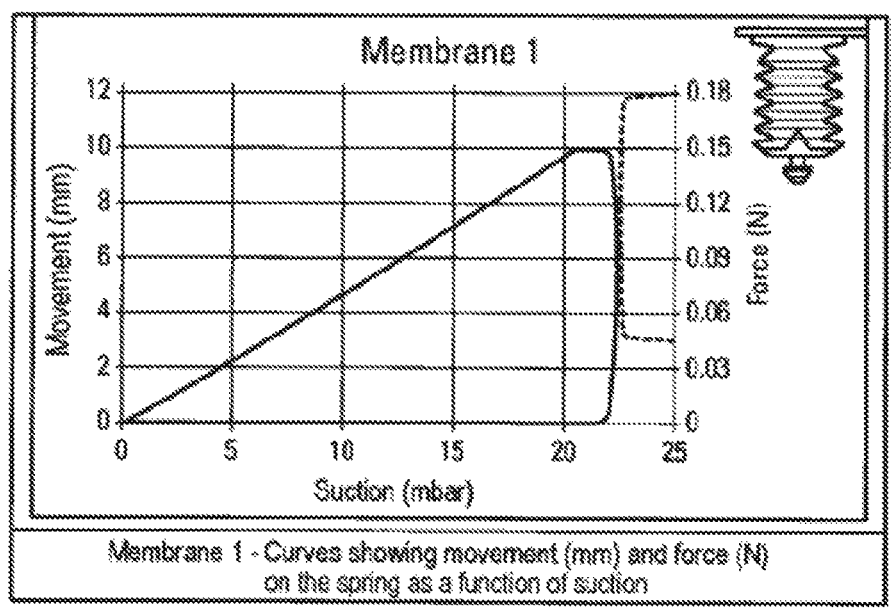
FIG. 15 plots curves showing force and movement as a function of suction in an air chamber in an advantageous embodiment of the invention.

In particular, as a result of having a closed chamber and a bellows shape, linear curves are obtained for force and movement as a function of suction, unlike air chambers of different shapes, e.g. formed by a deformable smooth membrane, for which such curves are much more random. FIG. 15 shows that the curves for an air chamber of the invention are indeed linear.

In all of the above-described embodiments, the blister strip is formed by a strip that presents two ends.

In a variant, a continuous strip could be used. Other modifications are also possible without going beyond the ambit of the present invention.

The present invention therefore makes it possible to provide a dry-powder inhaler that provides the following features:
  a plurality of individual doses of powder stored in individual sealed blisters, e.g. 30 or 60 doses stored on a rolled-up strip;

the powder is released by perforation that is achieved by the user inhaling, the blister being perforated by means of an inhalation detector system that is coupled to a prestressed release system;

appropriately-shaped drive means that are engaged with blisters so as to displace the blister strip after each inhalation, and bring a new full blister into a position in which it is to be opened by appropriate opening means;

means for avoiding doses being lost in the event of the inhaler being opened, but in the absence of any inhalation; and a dose indicator adapted to count the doses only in the event of inhalation.

Other features are also provided by the device of the invention as described above.

It should be observed that the various features, even if they are shown as being provided simultaneously on the inhaler, could be implemented separately.

In particular, the inhalation trigger mechanism could be used regardless of the type of reservoir opening means, regardless of the use of a dose indicator, regardless of the way in which the individual blisters are arranged relative to one another, etc.

The cocking means and the inhalation trigger system could be made in some other way.

The same applies for other component parts of the device.

Various modifications are also possible for the skilled person without departing from the scope of the present invention as defined in the accompanying claims. In particular, the various characteristics and functions of the device described with reference to the drawings can be combined together in any appropriate manner.

The invention claimed is:

1. A fluid dispenser device including a body and at least one individual reservoir containing a single dose of dispersible substance, opening means being provided for opening an individual reservoir each time the device is actuated, the device including an inhalation piece and an inhalation trigger system that comprises a deformable air chamber that co-operates with said inhalation piece, and a trigger element that co-operates with said air chamber, such that during inhalation through said inhalation piece, said air chamber is deformed and said trigger element actuates said opening means, so that a reservoir is opened by said opening means, said air chamber is a hollow pouch comprising: a deformable side body; an open first end including a peripheral edge that surrounds an opening forming an inlet of said hollow pouch; and a second end forming a bottom of said hollow pouch; said second end including connection means for connecting said air chamber to said trigger element, said side body being in the form of a bellows comprising a plurality of bellows portions arranged axially one after another, wherein said bellows in the side body comprises bellows portions having outside diameters that are different and having inside diameters that are different, wherein a first one of the bellows portions adjacent to said opening has a maximum outside diameter that is smaller than a maximum outside diameter of a second one of the bellows portions adjacent to said first one of the bellows portions.

2. The device according to claim 1, wherein said air chamber is a blind hollow pouch including a closed second end that forms the bottom of said hollow pouch.

3. The device according to claim 1, wherein said air chamber is connected to said inhalation piece and to a dispenser chamber which receives the dose of dispersible substance contained in a reservoir after the reservoir has been opened, said dispenser chamber containing at least one movable ball.

4. The device according to claim 1, including movable support means that are adapted to move an individual reservoir against said opening means on each actuation, said movable support means being displaceable between a non-dispensing position and a dispensing position, said movable support means being urged towards their dispensing position by resilient means and being held in their non-dispensing position by blocking means that are released by the user inhaling.

5. The device according to claim 4, wherein said trigger element co-operates with said blocking means so as to release said movable support means, which, once released, urge a reservoir against said opening means.

6. The device according to claim 4, wherein the resilient means is a spring or a spring blade.

7. The device according to claim 1, wherein said movable support means support a guide wheel, the reservoirs being made in the form of an elongate strip comprising a plurality of individual reservoirs disposed one behind another, said guide wheel causing said strip to advance each time the device is actuated.

8. The device according to claim 1, wherein said opening means include a perforator element that is adapted to cut a closure wall of the reservoir in such a manner that the cut portion(s) does/do not obstruct the opening(s) that is/are formed.

9. The device according to claim 1, wherein said air chamber is made of silicone rubber.

10. The device according to claim 1, wherein said connection means for connecting said air chamber to said trigger element comprise a projection that is formed on the outside of said deformable air chamber, said projection being snap-fastened on said trigger element while the device is being assembled.

11. The device according to claim 10, wherein said projection is snap-fastened in a hole of the trigger element.

12. The device according to claim 1, wherein said peripheral edge of the air chamber is heat-sealed on a portion of said body and/or overmolded on said portion of said body.

13. The device according to claim 12, wherein said peripheral edge of the air chamber is heat-sealed by ultrasound.

14. The device according to claim 1, wherein the plurality of bellow portions number six.

15. The device according to claim 1, wherein the dispersible substance is a fluid or a powder.

16. A fluid dispenser device including a body and at least one individual reservoir containing a single dose of dispersible substance, a perforator or cutter for opening an individual reservoir each time the device is actuated, the device including an inhalation piece and an inhalation trigger system that comprises a deformable air chamber that co-operates with said inhalation piece, and a trigger element that co-operates with said air chamber, such that during inhalation through said inhalation piece, said air chamber is deformed and said trigger element actuates said perforator or cutter, so that a reservoir is opened by said perforator or cutter, said air chamber is a hollow pouch comprising: a deformable side body; an open first end including a peripheral edge that surrounds an opening forming an inlet of said hollow pouch; and a second end forming a bottom of said hollow pouch; said second end including a projection for connecting said air chamber to said trigger element, said side body being in the form of a bellows comprising a plurality of bellows portions arranged axially one after another, wherein said bellows in the side body comprises bellows portions having outside diameters that are different and having inside diameters that are different, wherein a first one of the bellows portions adjacent to said opening has an outside diameter that is smaller than an outside diameter of one of the bellows portions further from said opening.

\* \* \* \* \*